(12) United States Patent
Suzuki et al.

(10) Patent No.: US 11,559,472 B2
(45) Date of Patent: Jan. 24, 2023

(54) BENTONITE AND SKIN TREATMENT COMBINATION METHOD AND PACKAGING

(71) Applicants: Terry Suzuki, Bellevue, WA (US); Lisa Suzuki, Bellevue, WA (US); Chelsea Suzuki, Bellevue, WA (US); Benjamin LaBelle, Victorville, CA (US)

(72) Inventors: Terry Suzuki, Bellevue, WA (US); Lisa Suzuki, Bellevue, WA (US); Chelsea Suzuki, Bellevue, WA (US); Benjamin LaBelle, Victorville, CA (US)

(*) Notice: Subject to any disclaimer, the term of this patent is extended or adjusted under 35 U.S.C. 154(b) by 225 days.

(21) Appl. No.: 16/936,073

(22) Filed: Jul. 22, 2020

(65) Prior Publication Data

US 2022/0023165 A1    Jan. 27, 2022

(51) Int. Cl.
*A61K 8/19* (2006.01)
*A61Q 19/00* (2006.01)
*A61K 8/02* (2006.01)

(52) U.S. Cl.
CPC .............. *A61K 8/19* (2013.01); *A61K 8/0212* (2013.01); *A61Q 19/00* (2013.01); *A61K 2800/87* (2013.01)

(58) Field of Classification Search
CPC .......... A61K 8/19; A61K 8/0212; A61K 8/26; A61K 2800/87; A61Q 19/00
See application file for complete search history.

(56) References Cited

U.S. PATENT DOCUMENTS

| 3,929,987 A | 12/1975 | Colodney et al. |
| 5,226,434 A | 7/1993 | Britton et al. |
| 5,840,320 A * | 11/1998 | Odom ...................... A61K 8/26 424/722 |

(Continued)

FOREIGN PATENT DOCUMENTS

| CN | 87 1 02386 A | 3/1987 |
| CN | 102078279 A | 6/2011 |

(Continued)

OTHER PUBLICATIONS

L'OREAL, Aug. 3, 2018, (https://www.lorealparisusa.com/beauty-magazine/skin-care/skin-care-essentials/how-to-apply-and-remove-a-clay-mask) (Year: 2018).*

(Continued)

*Primary Examiner* — Blessing M Fubara
(74) *Attorney, Agent, or Firm* — Averill & Green; Kenneth L. Green

(57) ABSTRACT

A skin treatment product and method includes steps of detoxifying cleansing, tightening, and moisturizing skin, by applying bentonite paste, followed by a skin moisturizer, to provide improved skin health and appearance. A single packaging contains bentonite paste and the skin moisturizer. The bentonite paste may be applied in a first step to extract oils, toxins, bacteria and other materials from the skin. After the bentonite paste dries and is removed, the moisturizer is applied to the skin, preferably a vitamin and/or mineral infused moisturizer. In one embodiment, the skin moisturizer is in the form of a skin mask. Following moisturizing the skin, a third step may be to nourish the skin. The skin treatment may be applied to facial skin, feet, hands, or any skin surface.

13 Claims, 3 Drawing Sheets

(56) References Cited

U.S. PATENT DOCUMENTS

| | | | | |
|---|---|---|---|---|
| 2005/0004508 A1* | 1/2005 | Sun | ............... | A61N 1/30 |
| | | | | 977/932 |
| 2006/0253078 A1* | 11/2006 | Wu | ............ | A61M 37/0015 |
| | | | | 604/173 |
| 2012/0192884 A1 | 8/2012 | Nasu et al. | | |
| 2013/0344131 A1* | 12/2013 | Lo | ............... | A61L 15/18 |
| | | | | 424/447 |

FOREIGN PATENT DOCUMENTS

| | | | | |
|---|---|---|---|---|
| CN | 104306677 A | | 1/2015 | |
| EP | 0 253 489 A2 | | 1/1988 | |
| EP | 2853260 A1 | * | 4/2015 | ......... A61K 31/4439 |
| WO | WO 2008/055815 A1 | | 5/2008 | |
| WO | WO-2020109481 A1 | * | 6/2020 | ........... A61K 8/0212 |

OTHER PUBLICATIONS

How to use a dry clay mask (https://facialclaymasks.com/how-to-use-a-clay-mask/) (Year: 2019).*
Colette Bouchez (https://www.medicinenet.com/script/main/art.asp?articlekey=50505) (Year: 205).*
Navin M. Geria, "What's Behind the Popularity of Today's Facial Masks?" in Anti-aging and Cosmeceutical Corner, vol. 52 Issue %, 46, 2016. (Year: 2016).*
RD 535028 A, published Nov. 10, 2008. (Year: 2008).*

* cited by examiner

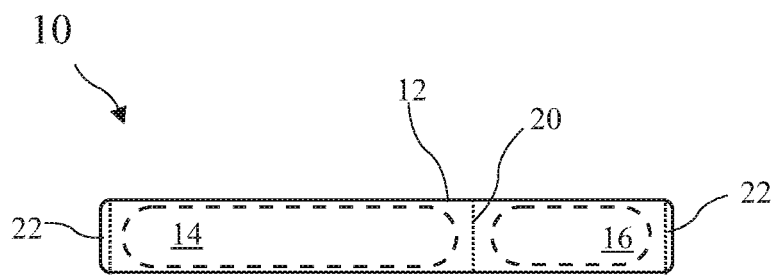
FIG. 1C
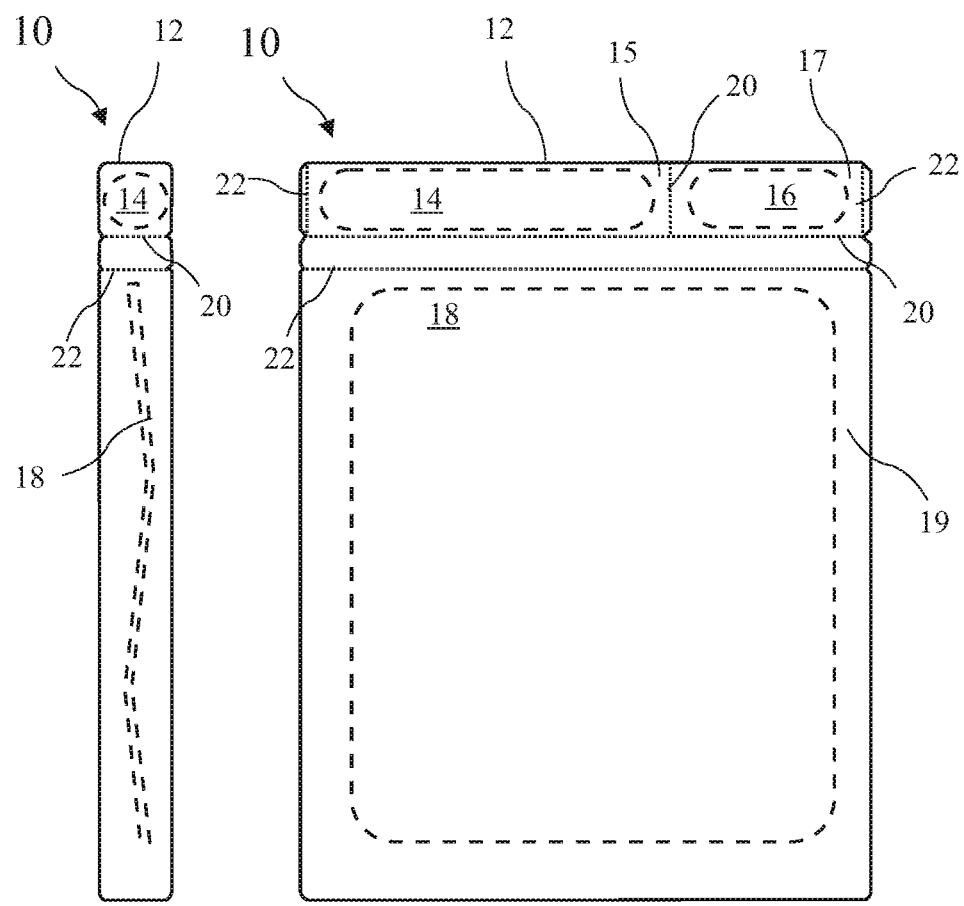
FIG. 1B
FIG. 1A

BENTONITE AND SKIN TREATMENT COMBINATION METHOD AND PACKAGING

BACKGROUND OF THE INVENTION

The present invention relates to skin treatments and in particular to packaging a bentonite paste and mask based skin treatment.

Skin health and appearance is an important issue to many people. Damaged skin is a source of embarrassment to many people. Various products and methods are available to improve skin health and appearance, but they do not provide a complete solution. Often products are not used in a manner to obtain the greatest benefit, for example, face masks applied to facial skin with blocked pores.

BRIEF SUMMARY OF THE INVENTION

The present invention addresses the above and other needs by providing a skin treatment product and method includes steps of detoxifying cleansing, tightening, and moisturizing skin, by applying bentonite paste, followed by a skin moisturizer, to provide improved skin health and appearance. A single packaging contains bentonite paste and the skin moisturizer. The bentonite paste may be applied in a first step to extract oils, toxins, bacteria and other materials from the skin. After the bentonite paste dries and is removed, the moisturizer is applied to the skin, preferably a vitamin and/or mineral infused moisturizer. In one embodiment, the skin moisturizer is in the form of a skin mask. Following moisturizing the skin, a third step may be to nourish the skin. The skin treatment may be applied to facial skin, feet, hands, or any skin surface.

In accordance with one aspect of the invention, there is provided a bentonite paste preferably made using calcium bentonite clay. Calcium bentonite does not dry out or dehydrate the skin as sodium bentonite can. The bentonite clay is mixed with water with between preferably a two to one and a three to one water to bentonite clay mixture by volume, and more preferably a 2.5 to one water to bentonite clay mixture by volume.

In accordance with another aspect of the invention, there is provided a skin treatment method. The method includes separating a bentonite paste portion of packaging from a mask portion, opening the bentonite paste portion of the packaging, applying bentonite paste to the skin, allowing the bentonite paste to dry and remove with warm water after 10 to 15 minutes, removing the dry bentonite paste with warm water, opening a moisturizing treatment of the packaging, applying the moisturizing treatment to the cleansed skin, removing the moisturizing treatment after 10 to 15 minutes if necessary. A preferred moisturizing treatment is a vitamin and mineral nourishing moisturizer to the skin.

In accordance with yet another aspect of the invention, there is provided a skin treatment method improving the effectiveness of moisturizing products. A first step of applying a bentonite paste removes impurities and toxins which reduce the effectiveness of a mask. A deep cleansing, tightening, and stretching effect of the bentonite paste also puts the skin in a very receptive condition for further moisturizing. The deep cleansing, tightening, and stretching allows following steps to be more effective and have a deeper therapeutic effect.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 1A is a front view of packaging of bentonite paste and a skin mask, according to the present invention.

FIG. 1B is a side view of the packaging of the bentonite paste and the skin mask, according to the present invention.

FIG. 1C is a top view of the packaging of the bentonite paste and the skin mask, according to the present invention.

Corresponding reference characters indicate corresponding components throughout the several views of the drawings.

DETAILED DESCRIPTION OF THE INVENTION

Figure 2C:
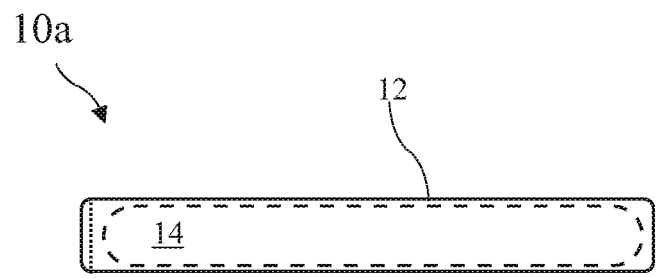
FIG. 2C is a top view of a second embodiment of the packaging of the bentonite paste and the skin mask, according to the present invention.

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement, or typically within 10 percent of a stated value.

A front view one embodiment of the present invention is a packaging 10 of bentonite paste 14 in a bentonite portion 15, a skin m ask 18 in a mask portion 19, and skin nourishment 16 in a nourishment product portion 17 according to the present invention is shown in FIG. 1A, a side view of the packaging 10 of the bentonite paste 14, the skin mask 18, and the skin nourishment 16 is shown in FIG. 1B, and a top view of the packaging 10 of the bentonite paste 14, the skin mask 18, and the skin nourishment 16 is shown in FIG. 1C. The packaging 10 is preferably a foil, plastic, paper, or paper with a plastic lining and includes tear lines 20 for separating bentonite portion 15, the third product portion 17 and the mask portion 19. Additional tear lines 22 at ends of the bentonite portion 15, nourishment product portion 17, and the m ask portion 19 are provided to release the bentonite 14, the moisturizer 16, and the mask 18. The tear lines 20 and 22 are preferably perforations. The tear line 22 in the mask portion 19 is preferably at the top of the mask portion 19.

The bentonite paste 14 is preferably calcium bentonite clay and is mixed with water with preferably between a two to one and a three to one water to bentonite clay mixture by volume, and more preferably about 2.5 to one water to bentonite clay mixture by volume, and most preferably 2.5 to one water to bentonite clay mixture by volume. Vitamin E may be added as a preservative.

The mask 18 is preferably a single use cloth mask impregnated with moisturizing serum. Known masks generally a fabric or non-woven fabric mask that conforms to the skin via slits on the mask, and provides a deep moisturizing treatment, generally stored and saturated in a pouch of essence/moisturizing solution. By having the mask on the skin, it helps maintain moisture on the skin for maximum absorption during the treatment. The known masks generally include a few basic ingredients with an infused herb, vitamin, or supplement. For example, a Green Tea face mask made by Bilidian in Korea has the following ingredients: purified water, glycerin, 1.3 butylene glycol, ethanol, hydrogenated oil, allantoin, imidazolidinyl urea, methyl, paraben, disodium edta, carbomer, triethanolamin, green tea, and a fragrance.

The skin nourishment 16 is preferably a vitamin and mineral nourishing moisturizer.

Figures 2A, 2B:
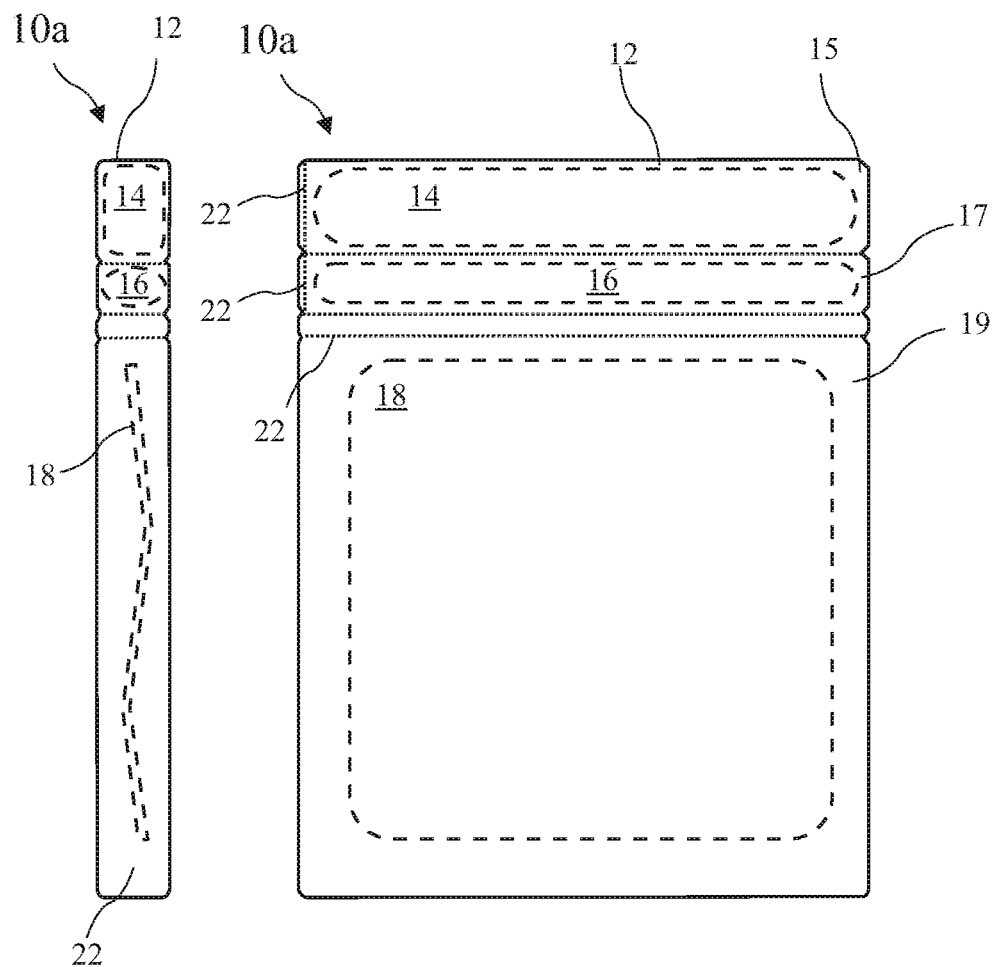
FIG. 2A is a front view of a second embodiment of packaging of the bentonite paste and the skin mask, according to the present invention.
FIG. 2B is a side view of a second embodiment of the packaging of the bentonite paste and the skin mask, according to the present invention.

A front view of a second embodiment of packaging 10a of the bentonite paste 14, the skin mask 18, and the moisturizer 16 according to the present invention is shown in FIG. 2A, a side view of the second embodiment of the packaging of the bentonite paste 14, the skin mask 18, and the moisturizer 16 is shown in FIG. 2B, and a top view of the second embodiment of the packaging of the bentonite paste 14, the skin mask 18, and the moisturizer 16 is shown in FIG. 2C. The packaging 10a is similar to the packaging 10, however, the moisturizer portion 17 is between the bentonite portion 15 and m ask portion 19.

Figure 3:
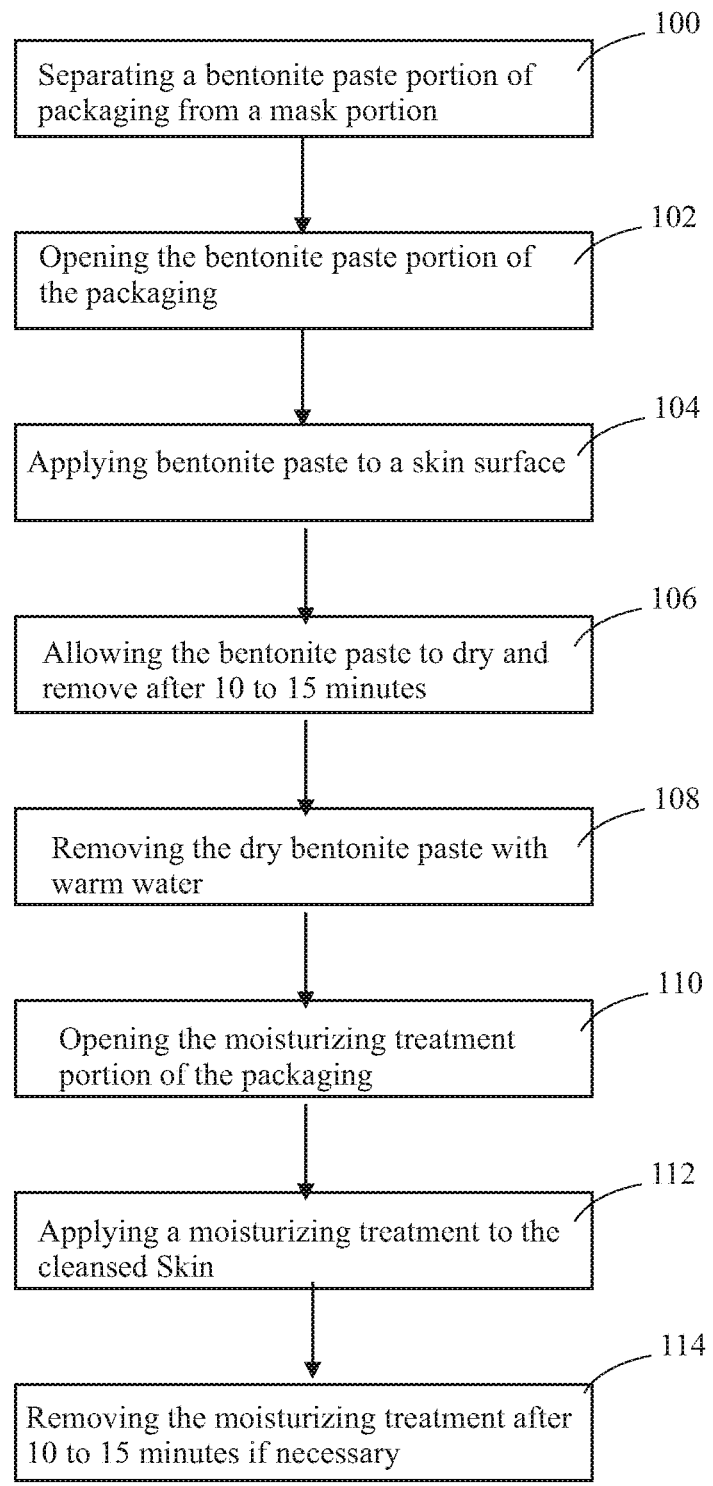
FIG. 3 is a method according to the present invention.

A method according to the present invention is shown in FIG. 3. The method includes separating a bentonite paste portion of packaging from a mask portion at step 100, opening the bentonite paste portion of the packaging at step 102, applying bentonite paste to a skin at step 104, allowing the bentonite paste to dry and remove with warm water after 10 to 15 minutes at step 106, removing the dry bentonite paste with warm water at step 108, opening the moisturizing treatment portion of the packaging at step 110, applying the moisturizing treatment to the cleansed skin at step 112, and removing the moisturizing treatment after 10 to 15 minutes if necessary at step 114. An additional step may include applying a vitamin and mineral nourishment to the skin.

The packaging is an inert, plastic airtight container, and is preferably a plastic material and more preferably PET, PE, or PP. The packaging may be a foil lined package having a PET plastic film layer, commonly referred to "cosmetics film".

While the invention herein disclosed has been described by means of specific embodiments and applications thereof, numerous modifications and variations could be made thereto by those skilled in the art without departing from the scope of the invention set forth in the claims.

We claim:

1. A skin care method comprising:
   separating a bentonite paste portion of packaging from a moisturizer portion;
   opening the bentonite paste portion of the packaging;
   applying bentonite paste to a skin;
   allowing the bentonite paste to dry to produce cleansed skin;
   removing the dry bentonite paste;
   opening the moisturizer portion of the packaging; and
   applying a moisturizer contained in the moisturizer portion to the cleansed skin,
   wherein the bentonite paste is calcium bentonite paste.

2. The method of claim 1, wherein applying a moisturizer comprises applying a skin mask to the skin.

3. The method of claim 1, wherein separating a bentonite paste portion of packaging from the moisturizer portion comprises separating a bentonite paste portion containing a bentonite paste comprising one part bentonite clay and between two and three parts water by volume.

4. The method of claim 3, wherein separating a bentonite paste portion containing a bentonite paste comprises separating a bentonite paste portion of packaging containing a bentonite paste comprising one part calcium bentonite clay and between two and three parts water by volume.

5. The method of claim 1, wherein separating a bentonite paste portion of packaging from a separating a bentonite paste portion containing a bentonite paste comprises separating a bentonite paste portion of packaging from a mask portion containing a bentonite paste comprising one part bentonite clay and about 2½ parts water by volume.

6. The method of claim 1, wherein the packaging is an inert plastic material and airtight.

7. The method of claim 6, wherein the plastic material is polyethylene (PE), polypropylene (PP) or polyethylene terephthalate (PET).

8. The method of claim 1, wherein removing the dry bentonite paste comprises removing the dry bentonite paste with warm water after 10 to 15 minutes of applying the bentonite paste to the skin.

9. The method of claim 1, wherein the packaging further includes a skin nourishment portion containing a vitamin and mineral skin nourishment, the method further including:
   removing the moisturizing mask after 10 to 15 minutes;
   opening the nourishment portion;
   releasing a vitamin and mineral skin nourishment from the nourishment portion; and
   applying the vitamin and mineral skin nourishment to the skin.

10. The method of claim 1, wherein the applying bentonite paste to the skin is a first step in the method.

11. The method of claim 1, wherein the applying bentonite paste to a skin comprises applying calcium bentonite paste to the skin as a first step in the method.

12. The method of claim 11, wherein removing the dry bentonite paste comprises using warm water to remove dry calcium bentonite paste from the face.

13. A skin care method comprising:
   separating a bentonite paste portion of packaging from at least one other portion selected from the group consisting of a mask portion and a nourishment portion by tearing along at least one first tear line comprising perforations;
   separating the mask portion of packaging from at least one other portion selected from the group consisting of the nourishment portion and the bentonite paste portion by tearing along a second tear line comprising second perforations;
   wherein the bentonite paste is calcium bentonite paste,
   opening the bentonite paste portion of the packaging;
   releasing bentonite paste from the bentonite past portion, the bentonite paste comprising a mixture of one part calcium bentonite and 2½ parts water by volume;
   applying bentonite paste to the skin;
   allowing the bentonite paste to dry;
   removing the dry bentonite paste with warm water after 10 to 15 minutes;
   opening the mask portion of the packaging;
   removing a moisturizing mask from the mask portion;
   applying the moisturizing mask to the skin;
   removing the moisturizing mask after 10 to 15 minutes;
   opening the nourishment portion;
   releasing a vitamin and mineral skin nourishment from the nourishment portion; and
   applying the vitamin and mineral skin nourishment to the skin.

* * * * *